United States Patent [19]

Förster et al.

[11] Patent Number: 5,436,232
[45] Date of Patent: Jul. 25, 1995

[54] PHARMACEUTICAL COMPOSITION FOR PERITONEAL DIALYSIS

[75] Inventors: Harald Förster; Fatima Asskali, both of Frankfurt am Main, Germany; Ernst Nitsch, Linz, Austria

[73] Assignee: Laevosan-Gesellschaft MBH, Donau, Austria

[21] Appl. No.: 178,537

[22] Filed: Jan. 7, 1994

Related U.S. Application Data

[63] Continuation in part of PCT/EP92/01551, filed July 9, 1992.

[51] Int. Cl.$^6$ ............... A61M 1/28; A61K 31/70; A61K 31/715
[52] U.S. Cl. ............... 514/60; 514/832; 514/833; 536/110; 536/124
[58] Field of Search ............... 536/107, 110, 124; 514/60, 832, 833

[56] References Cited

U.S. PATENT DOCUMENTS

| | | | |
|---|---|---|---|
| 2,362,282 | 11/1944 | Lindsay | 536/110 |
| 3,639,389 | 2/1972 | Hull | 536/110 |
| 3,793,065 | 2/1974 | Morrison et al. | 106/212 |
| 3,937,821 | 2/1976 | Irikura et al. | 514/832 |
| 3,962,465 | 6/1976 | Richter et al. | 426/578 |
| 3,998,753 | 12/1976 | Antoshkiv et al. | 252/363.5 |
| 4,061,610 | 12/1977 | Glowaky et al. | 536/110 |
| 4,211,865 | 7/1980 | Ferruti et al. | 536/49 |
| 4,609,640 | 9/1986 | Morishita et al. | 530/300 |
| 4,615,739 | 10/1986 | Clark et al. | 106/34 |
| 4,629,698 | 12/1986 | Nitsch et al. | 424/101 |
| 4,879,283 | 11/1989 | Belzer et al. | 514/60 |
| 5,006,140 | 4/1991 | Loercks et al. | 524/734 |
| 5,039,520 | 8/1991 | Hunter | 424/83 |
| 5,122,539 | 6/1992 | Abraham et al. | 514/563 |
| 5,200,398 | 4/1993 | Strasberg et al. | 514/23 |

Primary Examiner—Ronald W. Griffen
Attorney, Agent, or Firm—Nikaido, Marmelstein, Murray & Oram

[57] ABSTRACT

A pharmaceutical composition is described as well as the use of a starch ester for the production of such a pharmaceutical composition for peritoneal dialysis (CAPD) in particular for continuous ambulatory peritoneal dialysis. Starch esters which are particularly suitable are e.g. acetyl starch with a molecular weight ($\overline{Mw}$) of 100000 to 200000 Daltons and a molar substitution of 0.3 to 0.5. Using the compositions according to the invention it is possible to carry out peritoneal dialysis without damaging the peritoneal epithelium. In addition it is not stored in the organs.

20 Claims, 3 Drawing Sheets

PHARMACEUTICAL COMPOSITION FOR PERITONEAL DIALYSIS

CROSS REFERENCED TO RELATED APPLICATION

This application is a continuation-in-part of PCT International Application No. PCT/EP92/01551, filed Jul. 9, 1992, and designating the U.S.

DESCRIPTION

The invention concerns pharmaceutical compositions which contain a hydrocolloid and their use for peritoneal dialysis.

Peritoneal dialysis (PD) is a method of systemic lavage in temporary or chronic renal insufficiency. The function of the kidneys is to remove end-products of metabolism (urea or uric acid) or substances supplied with the diet (e.g. potassium) from the body. When there is a loss of kidney function this results in poisoning of the organism by accumulation of such substances if no substitute measures are taken. Apart from peritoneal dialysis, haemofiltration and haemodialysis (systemic lavage) also come into consideration as substitute measures for the partial or complete loss of kidney function. These alternatives to peritoneal dialysis are associated with a great deal of apparatus and with the availability of an access to a blood vessel which disadvantages for the patient.

In contrast peritoneal dialysis, in particular in the form of continuous ambulatory peritoneal dialysis (CAPD), has the advantage of less encroachment on the patients and lack of dependence on stationary apparatus. The disadvantage of conventional hyperosmolar peritoneal dialysis is damage to the peritoneal epithelium by the use of hyperosmolar solutions that are used to achieve an excretion of the desired substances from the blood into the peritoneal cavity. In conventional peritoneal dialysis it is necessary to achieve this effect by the addition of 1 to 5% by weight glucose or other osmotically active substances (e.g. sorbitol) to the lavage solution. The passage of glucose from the abdominal cavity into the organism has a nutritive effect which in some circumstances can be of considerable significance and is undesirable.

The object of the present invention is therefore to provide pharmaceutical compositions for peritoneal dialysis which avoid the aforementioned disadvantages of the previously common PD and in particular of continuous ambulatory peritoneal dialysis. This object is achieved by the present invention.

According to claim 1 the subject matter of the invention is a pharmaceutical composition for peritoneal dialysis containing a starch ester as the colloid-osmotically active substance in which the starch is substituted with acyl groups of monocarboxylic acids or dicarboxylic acids or mixtures of mono- and dicarboxylic acids each with 2 to 6 C atoms in an amount of 1 to 12% by weight in combination with a physiologically acceptable electrolyte and/or one or several other osmotically active substances.

Practical embodiments thereof are the subject matter of claims 2 to 7.

It is known that starch derivatives, dextrans and gelatins, preferably with a molecular weight $\geq 40000$, can be used as a blood plasma substitute (plasma expanders) (cf. e.g. U.S. Pat. Nos. 3,937,821; DE-A 33 13 600; "Römp Chemielexikon, 9th Volume, page 919, 1509).

It has now been found that starch esters as defined in claim 1 and which are distinguished by a high water binding capability are very well suited for use in peritoneal dialysis.

According to the invention it is possible by dispensing with hyperosmolar solutions or in the case of a combination with conventionally used osmotically active substances by substantially reducing the hyperosmolarity of the lavage solutions in particular by doing without glucose or by reducing the concentration of glucose as the previously most important component to achieve a milder dialysing effect without damaging the peritoneal epithelium and with a lower nutritive action. According to the invention the difference in the osmotic pressure or the difference in colloid osmotic pressure is not of importance as the effective force for the excretion of end-products of metabolism into the peritoneal cavity but rather the water binding capability of acyl starch in the peritoneal cavity. The hydrocolloid effect causes a binding of water in the peritoneal cavity, a so-called "solvent drag" which is comparable with the effect of an osmotic pressure difference. This "solvent drag" leads to an excretion of substances into the peritoneal cavity and thus exerts the dialysing effect.

The invention therefore also concerns the use of the aforementioned pharmaceutical composition according to the invention for peritoneal dialysis.

The molecular weight (weight average $\overline{Mw}$) is preferably $> 1000$ Daltons. The upper limit of the molecular weight range of the starch esters is in this case uncritical and is in particular dependent on the fact that they should not lead to deposits in the organism. The upper limit of molecular weight which also depends on the type of starch ester is usually ca. 1000000 Daltons. A molecular weight of ($\overline{Mw}$) of ca. 100000 to 200000 Daltons is preferably used.

The starch esters which are particularly preferred according to the invention are starch esters with a molar substitution of 0.1 to 1.5. Starch esters are esters with organic carboxylic acids and in particular with aliphatic mono- and dicarboxylic acids with 2 to 6 carbon atoms such as e.g. acetic acid, propionic acid, butyric acid, isobutyric acid and in particular acetic acid. The molar substitution MS is preferably 0.3 to 0.5. A particularly preferred starch ester according to the invention is acetyl starch, in particular with a molecular weight ($\overline{Mw}$) of 100000 to 200000 Daltons and a substitution MS of 0.3 to 0.5.

The pharmaceutical composition according to the invention for peritoneal dialysis also contains a physiologically acceptable electrolyte and/or another osmotically active substance. The concentration of starch ester is preferably 1 to 12% w/v, in particular 2 to 6% w/v relative to the total pharmaceutical composition.

Electrolytes which come into consideration as physiologically acceptable electrolytes are those which are usually used in compositions for peritoneal dialysis i.e. in particular for example sodium chloride, calcium chloride, salts of the lower carboxylic acids with 2 to 4 carbon atoms, in particular acetic acid.

The other osmotically active substance can be a lower molecular organic compound, in particular one which is used for example in conventional hyperosmolar peritoneal dialysis and preferably consists of polyvalent alcohols, monosaccharides, disaccharides such as e.g. glycerol, sorbitol, maltose and primarily glucose and/or amino acids.

The pharmaceutical compositions according to the invention can contain one or several starch esters according to the invention in combination with one or several of the osmotically active substances in water.

The starch esters used according to the invention can be produced according to the application with the title "Process for the production of starch esters for clinical, in particular parenteral use" of the same applicant, file number P 4123000.0. The production of the pharmaceutical composition is carried out in a known manner e.g. by mixing the components and the pharmaceutical vehicle, the starch ester being preferably used in the form of a powder obtained by drying, e.g. by spray drying, drum drying or vacuum drying, and grinding.

The invention therefore also concerns the use of a starch ester in which the starch is substituted with acyl groups of monocarboxylic acids or dicarboxylic acids or a mixture of mono- and dicarboxylic acids each with 2 to 6 C atoms for the production of a pharmaceutical composition for peritoneal dialysis according to claim 9. Practical embodiments of this use are set forth in the subclaims 10 to 15.

During dialysis the hydrocolloids used in the lavage solution pass from the peritoneal cavity into the blood. As a consequence those starch esters are especially suitable which are degraded in the organism and are thus not stored even in long-term treatment.

A particularly preferred starch ester according to the invention is acetyl starch. These starch esters can be degraded and metabolised by the action of endogenous enzymes. As a result of this physiological degradation glucose is also formed in addition to oligosaccharides, isomaltose and maltose. As a consequence it is also possible to carry out a peritoneal dialysis without the addition of glucose (glucose-free peritoneal dialysis). Part of the glucose formed during the degradation of the starch ester, such as acetyl starch, is excreted into the peritoneal cavity even during the dialysis and as a consequence it is possible to reduce the nutritive effect of peritoneal dialysis with starch esters. An influence of peritoneal dialysis carried out with starch ester on the fat metabolism of experimental animals was not detected. "Glucose-free peritoneal dialysis" therefore has major advantages compared to conventional peritoneal dialysis in which glucose solutions of higher percentage are used. In addition degradation by endogenous enzymes prevents storage of starch esters. In contrast to hydroxyethyl starch even after a 5 day peritoneal dialysis with acetyl starch no polysaccharide was detected in high concentrations in the organs of the examined experimental animals.

The aforementioned results are based on animal experiments on bilaterally nephrectomized rats. The blood of the animals was purified of urea as a reference substance or of corresponding electrolytes (e.g. potassium) by use of a 3% acetyl starch solution with addition of appropriate electrolytes. The animals could be maintained in an adequate state of health by daily peritoneal dialysis over a period of 5 days. Comparative experiments were carried out with solutions which contained glucose (2% w/v). In addition investigations were carried out with solutions which contained a combination of acetyl starch according to the invention with 1% by weight glucose as the other osmotically active substance. Dialysis effects were observed in all cases which were not only due to differences in the osmotic or in the colloid osmotic pressure. An approximation of the plasma concentration and lavage solution concentration was also achieved by using isomolar hydrocolloid solutions according to the invention (i.e. without osmotically active gradients). This therefore proves that the hydrocolloid effect causes a binding of water in the peritoneal cavity and exerts a dialysing effect by means of the so-called "solvent drag" which corresponds to that of an osmotic pressure difference.

Even after a 5 day successful peritoneal dialysis with acetyl starch solutions only traces of acetyl starch were detected in the serum of the dialysed animals (cf. FIG. 1). When the organs were examined acetyl starch was detected neither in the spleen nor in the liver or lungs. It can therefore be concluded from these investigations that acetyl starch which enters the blood circulation during the peritoneal dialysis is rapidly and completely degraded by endogenous enzymes.

It is intended to elucidate the invention in more detail by the following examples.

Example 1

Production of acetyl starch (AST) solutions for continuous ambulatory peritoneal dialysis (CAPD)

250 ml of each of the CAPD solutions listed in the following Table 2 were prepared. The electrolyte mixture stated in Table 1 was used for this. Acetyl amylopectin with a molar substitution MS of 0.355 and a Mw of ca. 200000 Daltons was used as the acetyl starch (AST). The solutions were dispensed into 20 ml piercing vials.

Table 2 shows that the solutions prepared in this way have a good stability. Even after sterilisation there was only a negligible saponification of the ester groups.

TABLE 1

| (Electrolyte mixture for CAPD solutions with AST) | | | |
|---|---|---|---|
| M | | mmol/l | g/l |
| 58.443 | sodium chloride | 120 | 7.013 |
| 136.080 | Na acetate.3H$_2$O | 25 | 3.402 |
| 147.020 | Ca chloride.2H$_2$O | 2 | 0.294 |
| 60.053 | acetic acid | 5 | 0.303 |
| osmolarity mOsmol/l | | 301 | |

TABLE 2

| | | | | | (CAPD solutions with AST) | | | | | |
|---|---|---|---|---|---|---|---|---|---|---|
| | AST | Gluc | | | acetic acid free esterif. | | residual acetyl groups. | | | |
| No. | g/l | g/l | mOsmol/l | pH | mmol/l | mmol/l | mol/mol | Mw · 10$^{-3}$ | *Mn · 10$^{-3}$ | |
| 1/1 | 30 | — | 301 | 5.49 | 3.28 | 53.66 | — | 313 | 153 | before steril. |
| | | | | 5.25 | 5.34 | 51.51 | 0.96 | 230 | 140 | 30'100° |
| | | | | 4.85 | 11.49 | 45.17 | 0.84 | 219 | 134 | 8'121° |
| 1/2 | 30 | 0.901 | 306 | 5.44 | 3.28 | 53.88 | — | 306 | 155 | before steril. |
| | | | | 5.21 | 5.44 | 51.51 | 0.96 | 233 | 142 | 30'100° |
| | | | | 4.86 | 11.49 | 46.24 | 0.86 | 216 | 134 | 8'121° |
| 2/1 | 45 | — | 301 | 5.46 | 3.39 | 78.61 | — | 325 | 153 | before steril. |
| | | | | 5.19 | 5.95 | 76.68 | 0.98 | 203 | 130 | 30'100° |

TABLE 2-continued

| | | | | | (CAPD solutions with AST) | | | | |
|---|---|---|---|---|---|---|---|---|---|
| No. | AST g/l | Gluc g/l | mOsmol/l | pH | acetic acid free esterif. mmol/l | mmol/l | residual acetyl groups. mol/mol | $Mw \cdot 10^{-3}$ | $Mn \cdot 10^{-3}$ |
| 2/2 | 45 | 0.901 | 306 | 4.79 | 14.06 | 70.01 | 0.89 | 223 | 136 | 8'121° |
| | | | | 5.48 | 3.39 | 78.29 | — | 275 | 147 | before steril. |
| | | | | 5.18 | 6.36 | 76.14 | 0.97 | 218 | 136 | 30'100° |
| | | | | 4.81 | 14.06 | 68.72 | 0.88 | 226 | 138 | 8'121° |

*The higher $\overline{Mw}$'s and $\overline{Mn}$'s before sterilization are probably mainly due to formation of aggregates.

All solutions were almost colourless even after the sterilization. As expected the sterilization caused a slight acetyl cleavage. The residual acetyl content was ca. 96% in a mild sterilization (30 min at 100° C.) and ca. 86% after sterilization for 8 minutes at 121° C. It is therefore expedient to carry out a mild sterilization.

The following further solutions according to the invention for peritoneal dialysis using the electrolytes stated in Table 1 were prepared in a similar manner:

1. 3% acetyl starch solution (molar substitution 0.3 or 0.5)
2. Combination solution with 1.5% acetyl starch and 1% glucose (as an example of an osmotically active substance)
3. 3% hydroxyethyl starch solutions HES with 200/0.5 (weight average of the molecular weight ca. 200000 Daltons, molar substitution 0.5 mol), HES 100/0.7, HES 40/0.5, HES 70/0.7 and HES 450/0.7.
4. 3% hydroxyethyl starch solutions (HES 40/0.5 and HES 200/0.5) with 1% glucose.

Example 2

Procedure for peritoneal dialysis

Wistar rats with a body weight of 250 to 350 g are bilaterally nephrectomized under anaesthesia. In addition two indwelling catheters with external leads are surgically introduced into the abdominal cavity. As a substitute for kidney function 6 to 8 lavages of the abdominal cavity are carried out by introducing 60 to 100 ml lavage solution in each case. After a period of 30 to 60 minutes in each case, the lavage solution is drained off.

With this treatment it is possible to keep the animals alive and in good health over longer periods despite the lack of kidneys. 5 dialysis days were chosen as the experimental period. On the 5th day blood samples were taken from the orbita immediately before the start of dialysis. After the last dialysis of the day the animals were killed under anaesthesia by exsanguination from the abdominal aorta. Subsequently the following organs were excised for further examinations: spleen, liver, lungs.

Figure 1:
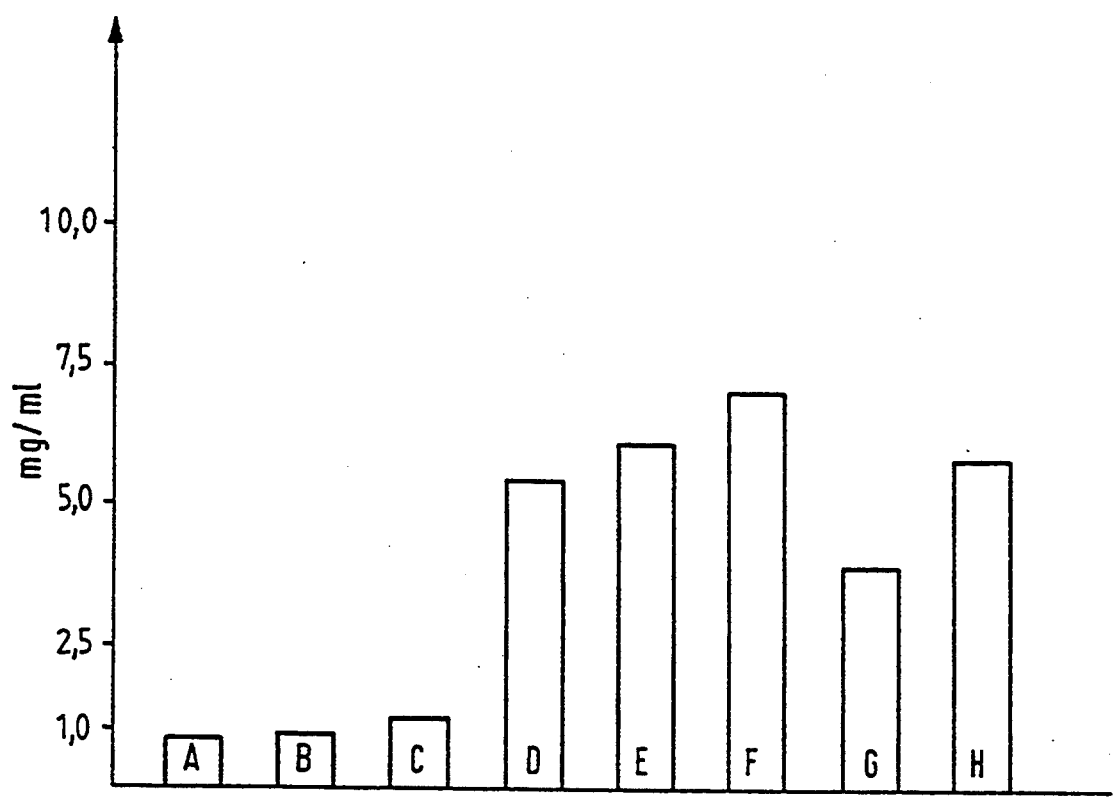
FIG. 1 shows the serum content (in mg/ml) after the 5th dialysis (5th day).
Figure 2:
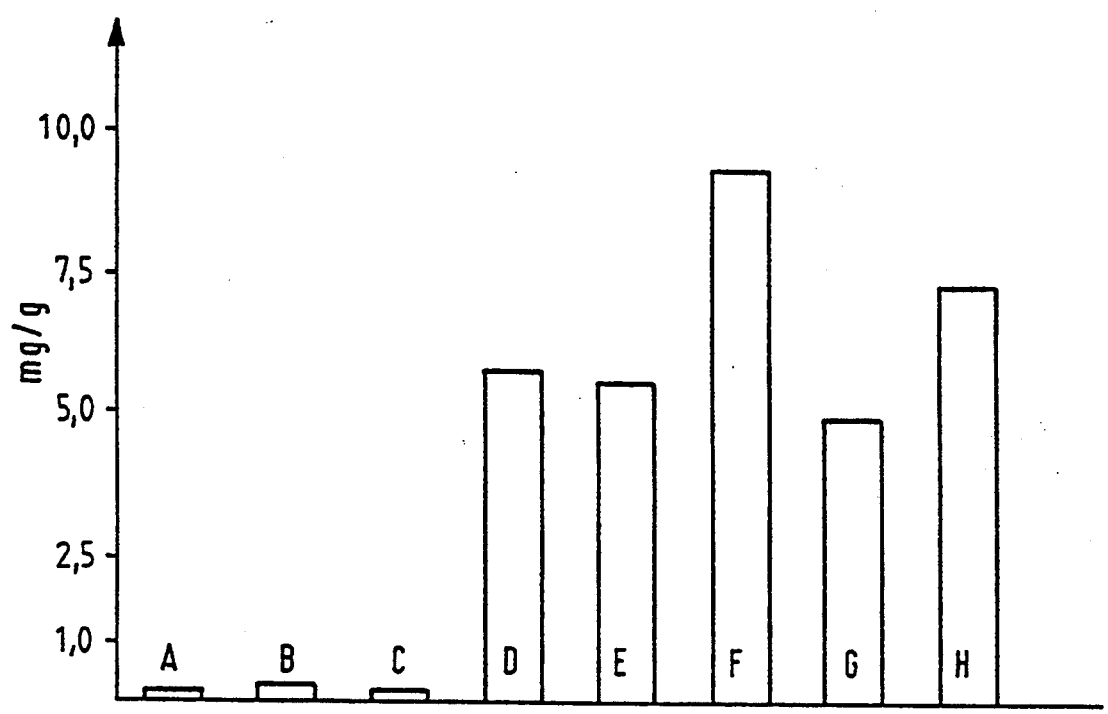
FIG. 2 shows the content of hydrocolloid in the spleen (in mg/g) after the 5th dialysis (5th day).

In FIG. 1 and 2 A, B, C denote: 3% acetyl starch (acetylamylopectin) solutions without addition of glucose, D to H denote: 3% hydroxyethyl starch solutions without addition of glucose and namely with HES 100/0.7 (D), HES 40/0.5 (E), HES 70/0.7 (F), HES 200/0.5 (G) and HES 450/0.7 (H).

Figure 3:
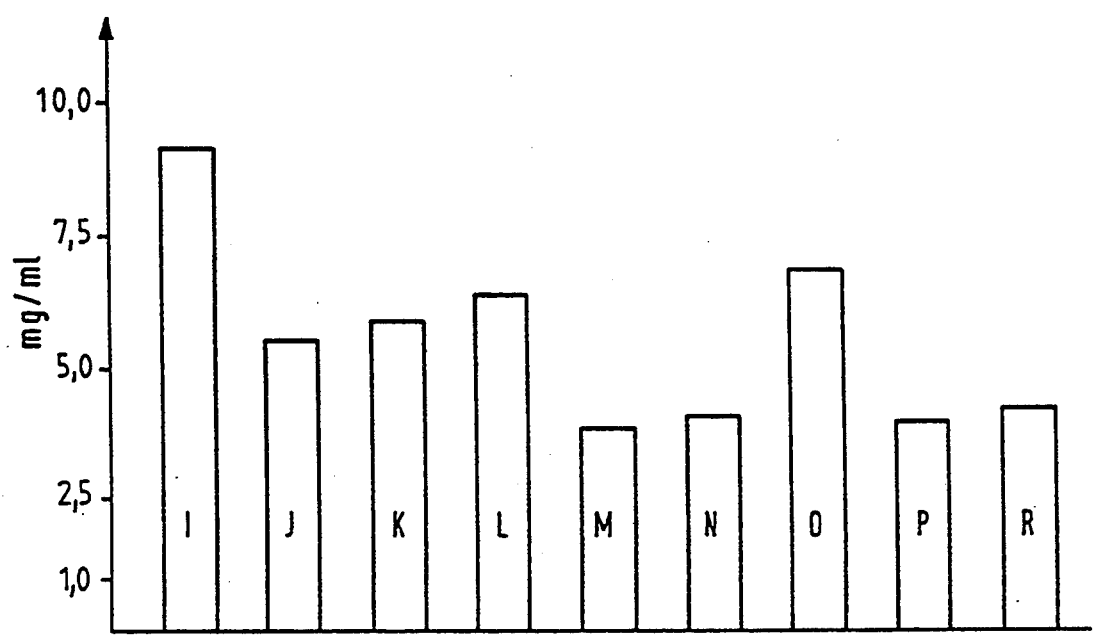

FIG. 3 shows the urea content in the serum before and after the 5th dialysis (5th day) and in the dialysate.

I, J, K denote: 3% acetyl starch solution without glucose (extraction 36%) and namely the serum content before dialysis (I), after dialysis (J) and in the dialysate (K);

L, M, N denote: 3% HES 40/0.5 solution with 1% glucose (extraction 39.4%) and namely the serum content before dialysis (L), after dialysis (M) and in the dialysate (N);

O, P, R denote: 3% HES 200/0.5 solution with 1% glucose (extraction 42%) and namely the serum content before dialysis (O), after dialysis (P) and in the dialysate (R).

We claim:

1. A pharmaceutical composition for peritoneal dialysis consisting essentially of a starch ester in an amount of 1 to 12% by weight as a colloid-osmotically active substance, in combination with at least one component selected from the group consisting of a physiologically acceptable electrolyte and one or more other osmotically active substances,
   wherein said starch ester is substituted with acyl groups of monocarboxylic acids with 2 to 6 C atoms, dicarboxylic acids with 2 to 6 C atoms or mixtures of said mono- and dicarboxylic acids.

2. The pharmaceutical composition according to claim 1, wherein said starch ester has a molecular weight (Mw) of more than 1000 Daltons and a molar substitution of 0.1 to 1.5.

3. The pharmaceutical composition according to claim 2, wherein said starch ester has a molecular weight (Mw) of 100,000 to 200,000 Daltons.

4. The pharmaceutical composition according to claim 2, wherein said starch ester has a molar substitution of 0.3 to 0.5.

5. The pharmaceutical composition according to claim 1, wherein said starch ester is acetyl starch.

6. The pharmaceutical composition according to claim 5, wherein said acetyl starch has a molecular weight (Mw) of 100,000 to 200,000 Daltons and a molar substitution of 0.1 to 0.7.

7. The pharmaceutical composition according to claim 6, wherein said acetyl starch has a molar substitution of 0.3 to 0.5.

8. The pharmaceutical composition according to claim 1, wherein said starch ester is in an amount of 2 to 6% by weight.

9. The pharmaceutical composition according to claim 1, wherein the other osmotically active substances are selected from the group consisting of polyvalent alcohols, monosaccharides, disaccharides and amino acids.

10. The pharmaceutical composition according to claim 9, wherein said other osmotically active substance is glucose.

11. A method for purifying blood, comprising carrying out peritoneal dialysis with a composition comprising a starch ester in solution,
wherein said starch ester is substituted with acyl groups of monocarboxylic acids with 2 to 6 C atoms, dicarboxylic acids with 2 to 6 C atoms or mixtures of said mono- and dicarboxylic acids.

12. The method according to claim 11, wherein said starch ester has a molecular weight of more than 1000 Daltons and a molar substitution (Ms) of 0.1 to 1.5.

13. The method according to claim 12, wherein said starch ester has a molecular weight of 100,000 to 200,000 Daltons.

14. The method according to claim 12, wherein said starch ester has a molar substitution (Ms) of 0.3 to 0.5.

15. The method according to claim 11, wherein said starch ester is acetyl starch.

16. The method according to claim 15, wherein said acetyl starch has a molecular weight of 100,000 to 200,000 Daltons and a molar substitution of 0.1 to 0.7.

17. The method according to claim 15, wherein said acetyl starch has a molar substitution of 0.3 to 0.5.

18. The method according to claim 11, further comprising administering at least one substance selected from the group consisting of a physiologically acceptable electrolyte and another osmotically active substance.

19. The method according to claim 18, wherein said osmotically active substance is selected from the group consisting of a polyvalent alcohol, a monosaccharide, a disaccharide and an amino acid.

20. The method according to claim 19, wherein said osmotically active substance is glucose.

* * * * *